(12) United States Patent
Lee

(10) Patent No.: US 9,687,695 B2
(45) Date of Patent: Jun. 27, 2017

(54) METHODS AND SYSTEMS FOR TRAINING PROPER RUNNING OF A USER

(71) Applicant: Dalsu Lee, Toronto (CA)

(72) Inventor: Dalsu Lee, Toronto (CA)

(73) Assignee: Dalsu Lee, Mississauga (CA)

( * ) Notice: Subject to any disclaimer, the term of this patent is extended or adjusted under 35 U.S.C. 154(b) by 337 days.

(21) Appl. No.: 14/520,472

(22) Filed: Oct. 22, 2014

(65) Prior Publication Data

US 2016/0114213 A1 Apr. 28, 2016

(51) Int. Cl.
| | | |
|---|---|---|
| A63B 24/00 | (2006.01) | |
| A61B 5/00 | (2006.01) | |
| A61B 5/11 | (2006.01) | |

(52) U.S. Cl.
CPC ........ *A63B 24/0075* (2013.01); *A61B 5/1118* (2013.01); *A61B 5/6802* (2013.01); *A61B 5/744* (2013.01); *A61B 2503/10* (2013.01)

(58) Field of Classification Search
CPC ............ A63B 24/0062; A63B 24/0075; A63B 2024/0012; A63B 2024/0168; A63B 2024/0171; A61B 2562/0219; A61B 5/6802; A61B 5/744; A61B 5/1118; A61B 2503/10
See application file for complete search history.

(56) References Cited

U.S. PATENT DOCUMENTS

| | | |
|---|---|---|
| 7,200,517 B2 | 4/2007 | Darley et al. |
| 7,264,554 B2 | 9/2007 | Bentley et al. |
| 7,771,320 B2 | 8/2010 | Riley et al. |
| 8,060,337 B2 | 11/2011 | Kulach et al. |
| 8,086,421 B2 | 12/2011 | Case, Jr. et al. |
| 8,200,323 B2 | 6/2012 | DiBenedetto et al. |
| 8,221,290 B2 | 7/2012 | Vincent et al. |
| 8,314,840 B1 | 11/2012 | Funk |
| 8,382,688 B2 | 2/2013 | Dar et al. |

(Continued)

FOREIGN PATENT DOCUMENTS

| | | |
|---|---|---|
| CN | 102921162 A | 2/2013 |
| EP | 2650807 | 10/2013 |

OTHER PUBLICATIONS

Physical Simulation for Probabilistic Motion Tracking; Vondrak, M.; Sigal, L.; Jenkis, O.C.; Computer Vision and Pattern Recognition, 2008, CVPR 2008, IEEE Conference on, vol. No., pp. 1,8, Jun. 23-28, 2008; URL:http://ieeexplore.ieee.org/stamp/stamp.jsp?tp=&arnumber=4587580&isnumber=4587335.

(Continued)

*Primary Examiner* — Timothy A Musselman
(74) *Attorney, Agent, or Firm* — Ridout & Maybee LLP

(57) ABSTRACT

A method and system for training proper running of a user, the system including at least one inertial sensor, a memory, a controller, and an output interface. The memory is for storing information for an ideal running gait, the information including information for an ideal bounce or acceleration over time. The method can be implemented by the controller and includes displaying an animation of an ideal running gait and an actual running gait of the user, both simultaneously with cadence synchronized, and also providing to the output interface a comparison of an actual bounce of the user with the ideal bounce.

23 Claims, 9 Drawing Sheets

(56) References Cited

U.S. PATENT DOCUMENTS

| | | | |
|---|---|---|---|
| 8,460,001 B1* | 6/2013 | Chuang | G09B 19/0038 434/247 |
| 8,568,278 B2 | 10/2013 | Riley et al. | |
| 8,573,982 B1 | 11/2013 | Chuang | |
| 8,622,795 B2 | 1/2014 | Edis et al. | |
| 8,702,430 B2 | 4/2014 | DiBenedetto et al. | |
| 8,715,139 B2 | 5/2014 | DiBenedetto et al. | |
| 2008/0258921 A1 | 10/2008 | Woo et al. | |
| 2009/0023556 A1* | 1/2009 | Daly | A63B 22/0235 482/9 |
| 2010/0331145 A1 | 12/2010 | Lakovic et al. | |
| 2011/0311955 A1 | 12/2011 | Forsten et al. | |
| 2013/0190657 A1 | 7/2013 | Flaction et al. | |
| 2013/0192071 A1 | 8/2013 | Esposito et al. | |
| 2013/0244211 A1 | 9/2013 | Dowling et al. | |
| 2014/0188257 A1 | 7/2014 | Ura et al. | |
| 2014/0336003 A1 | 11/2014 | Franz et al. | |
| 2015/0025816 A1* | 1/2015 | Ross | A43B 17/00 702/44 |
| 2015/0081245 A1 | 3/2015 | Nagasaka | |
| 2016/0058373 A1* | 3/2016 | Anandabairavasamy | A61B 5/4866 600/595 |

OTHER PUBLICATIONS

Three-Dimensional Human Running; Hodgins, J.K.; Robotics and Automation, 1996. Proceedings., 1996 IEEE International Conference on, vol. 4, No., pp. 3271,3276 vol. 4, Apr. 22-28, 1996; URL:http://ieeexplore.ieee.org/stamt/stamp.jsp?tp=&arnumber=509211&isnumber=10818.

Illustrating the ideal running gait motion (Walking gait during training, warm-up) by making use of animation (http://en.wikipedia.org/wiki/Gait; Print date Jun. 19, 2014.

Gait analysis; from Wikipedia, the free encyclopedia; http://en.wikipedia.org/wiki/Gait_analysis; Print date Jun. 19, 2014.

Fitness Activity Tracker Comparison Chart; http://www.bestfitnesstrackerreviews.com/comparison-chart.html; Copyright (C) 2013 to present Best Fitness Tracker Reviews.

How to Achieve a Runner's High; by K. Aleisha Fetters; Published Apr. 25, 2014; http://www.runnersworld.com/running-tips/getting-high-endocannabinoids.

Why Do I Get Headaches After Running?; Christine Luff; Jun. 11, 2010; http://running.about.com/b/2010/06/11/why-do-i-get-headaches-after-running.htm.

Sweat Science; The Biomechanical Case for Minimalist Running; Can we draw any conclusion from force measurements?; Alex Hutchinson; Published May 13, 2013; http://m.runnersworld.com/barefoot-running-minimalism/the-biomechanical-case-for-minimalist-running.

* cited by examiner

Frame 5

Ideal 410    Test 411

Frame 6

Ideal 412    Test 413

Frame 7

Ideal 414    Test 415

Frame 8

Ideal 416    Test 417

Frame 9

Ideal 418    Test 419

Frame 10

Ideal 420    Test 421

Frame 11

Ideal 422    Test 423

Frame 12

Ideal 424    Test 425

◊ - Vertical
☐ - Forward (Direction of running)
△ - Side to Side

◊ - Ideal
☐ - Test Subject

METHODS AND SYSTEMS FOR TRAINING PROPER RUNNING OF A USER

TECHNICAL FIELD

At least some example embodiments relate to exercise instruction and, more particularly, to methods and systems for training proper, safe and more enjoyable running.

BACKGROUND

Running can be considered a complete form of fitness exercise but doctors usually recommend walking instead because of the risk of injury associated with running. Many people try running but unfortunately experience injury, which prevents them from continuing and trying again.

Typical running injuries occur in the knees, ankles and the lower leg, which are the weaker parts of weight bearing structure. This is true even for people who have been running for many years.

Many conventional systems for running training rely upon load/pressure applied to bottom of the foot/shoes, heel strike or toe strike, angle of landing, or amount of breaking during landing. Other systems may rely upon motions or stresses of the leg or foot, when assessing proper or ideal running patterns. One major goal for these types of systems is to merely minimize landing impact to reduce lower body forces.

Yet some other existing systems attempt to teach the runner proper technique based on minimizing any vertical bounce or displacement. A goal for this type of system is merely to minimize undesirably exerting unnecessary energy in a vertical upwards direction.

Additional difficulties with existing systems may be appreciated in view of the Detailed Description of Example Embodiments, below.

SUMMARY

In accordance with an example embodiment, there is generally provided a method and system for training proper running of a user, including providing an animation displays an ideal running gait and an actual running gait of the user, both simultaneously with cadence synchronized, and providing a comparison determination of an actual bounce or acceleration over time of the user with the ideal bounce or acceleration.

In accordance with another example embodiment, there is provided a system for training proper running of a user, including: at least one inertial sensor for attachment to an upper body of the user and configured to provide sensor data; at least one output interface including a display output interface; memory for storing information for an ideal running gait, the information including animation information and including information for an ideal acceleration over time which correlates to at least a GRF (Ground Reaction Force); and at least one processor in operable communication with the at least one inertial sensor, the output interface, and the memory, for executing instructions stored in the memory which, when executed, cause the at least one processor to: determine the ideal running gait information from the memory, determine the sensor data from the at least one inertial sensor for an actual running gait of the user, perform a comparison determination including: whether a rate of change of the actual acceleration of the user during ground impact is less than a predetermined value or within a threshold thereof, and whether a ground impact period of acceleration is greater than a predetermined value or within a threshold thereof, output to the at least one output interface information based on the comparison determination, and display on the display output interface an animation of the ideal running gait and the actual running gait, both simultaneously with cadence synchronized.

In accordance with another example embodiment, there is provided method for training proper running of a user, wherein at least one inertial sensor is for attachment to an upper body of the user and configured to provide sensor data, wherein at least one output interface includes a display output interface, wherein memory is for storing information for an ideal running gait, the information including animation information and including information for an ideal acceleration over time which correlates to at least a GRF (Ground Reaction Force), and wherein at least one processor is in operable communication with the at least one inertial sensor, the output interface, and the memory, for executing instructions stored in the memory, the method being executed by the at least one processor and comprising determining the ideal running gait information from the memory; determining the sensor data from the at least one inertial sensor for an actual running gait of the user; performing a comparison determination including: whether a rate of change of the actual acceleration of the user during ground impact is less than a predetermined value or within a threshold thereof, and whether a ground impact period of acceleration is greater than a predetermined value or within a threshold thereof; outputting to the at least one output interface information based on the comparison determination; and displaying on the display output interface an animation of the ideal running gait and the actual running gait, both simultaneously with cadence synchronized.

In accordance with another example embodiment, there is provided a non-transitory computer-readable medium containing instructions executable by a processor for training proper running of a user, wherein at least one inertial sensor is for attachment to an upper body of the user and configured to provide sensor data, wherein at least one output interface includes a display output interface, wherein memory is for storing information for an ideal running gait, the information including animation information and including information for an ideal acceleration over time which correlates to at least a GRF (Ground Reaction Force), and wherein at least one processor is in operable communication with the at least one inertial sensor, the output interface, and the memory, for executing instructions stored in the memory which, the instructions comprising: instructions for determining the ideal running gait information from the memory; instructions for determining the sensor data from the at least one inertial sensor for an actual running gait of the user; instructions for performing a comparison determination including: whether a rate of change of the actual acceleration of the user during ground impact is less than a predetermined value or within a threshold thereof, and whether a ground impact period of acceleration is greater than a predetermined value or within a threshold thereof; instructions for outputting to the at least one output interface information based on the comparison determination; and instructions for displaying on the display output interface an animation of the ideal running gait and the actual running gait, both simultaneously with cadence synchronized.

BRIEF DESCRIPTION OF THE DRAWINGS

Reference will now be made, by way of example, to the accompanying drawings which show example embodiments, in which.

Similar reference numerals may be used in different figures to denote similar components.

DETAILED DESCRIPTION OF EXAMPLE EMBODIMENTS

Figure 1:
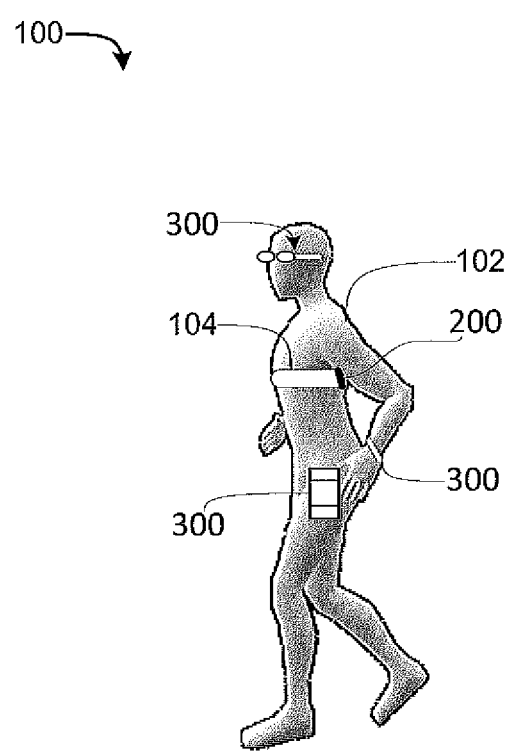
FIG. 1 diagrammatically shows an example system for training proper running of a user, in accordance with an example embodiment.

The running gait motion can be fundamentally broken down into four keys phases: 1) foot landing, initial contact; 2) landing impact absorption; 3) mid stance; and 4) propulsion/jumping. Most mistakes in training running come from trying to reduce the load on the foot, which causes lack of proper bounce or acceleration over time. Normally, a runner cannot escape from gravity so lack of proper bounce causes tendencies to use and stress the lower leg more than required, causing more strain. When repeated, this leads to injuries.

Proper running requires proper bounce, which needs proper coiling and compression of the body before propulsion. For example, if there is no coiling and compressing then there cannot be a smooth and stress-free propulsion.

The above mentioned coiling and compression of the body occurs between foot landing and mid stance. It is a very natural, comfortable way of absorbing the impact of landing. The crucial parts of the weight bearing structure in the body for coiling, compression and propulsion is found between the shoulder/arm and knee. The amount of coiling, compression and propulsion capable in the lower leg cannot match or replace what can and should happen in the body as described above. The fortunate fact for runners is that the body components that allow coiling and compression between the shoulder/arm and knee are orders of magnitude stronger than what is available in the lower leg. Taking advantage of this mechanical fact leads to a more natural, enjoyable running experience with reduced risk of injury. This will help people enjoy running as much as walking, can provide proper running training.

The major part of the above bounce (which absorbs the landing impact and makes the body airborne) should be done while the bottom of foot is firmly placed on the ground so that lower leg can be relatively relaxed even during the peak load and the impact of the initial landing (initial contact with ground) can be minimized. If this is not the case then the lower leg has to bear the load with extra stress often during the initial landing which often leads to injury. The above features of the running motion can allow proper, safer and more enjoyable running through a system and device providing precise control of movement, timing and continuous monitoring with feedback.

The precise control and timing of this movement linking the lower part of the weight/load bearing structures and the body is not easy, especially considering what is required. In many conventional systems, attention is usually given to lower leg only. Instead, a method described herein is to control precise movement and timing is making use of the upper body. For example, it is intuitive that controlling the upper body is much easier than to precisely control the motion of the lower body, for example, the user can perform much more precise movements with their hands than with their feet.

The specific positioning and movements of the shoulders, arms, hands and upper torso leads to proper movements in the lower part of weight/load bearing structures, such as legs and feet. This upper body control is much easier to teach and train than trying to train/teach how to move just the legs and feet.

For example, many existing systems only try to measure real time load/pressure applied to bottom of the foot/shoes, heel strike or toe strike, angle of landing, or amount of breaking during landing.

In accordance with an example embodiment, there is generally provided a method and system for training safe and more enjoyable running, including providing an animation which displays an ideal running gait and an actual running gait of a user, both simultaneously with cadence synchronized, and providing a comparison determination of an actual bounce or acceleration of the user with the ideal bounce.

In some example embodiments, the ideal bounce can include a soft landing including forefoot strike to the ground. In some example embodiments, the ideal bounce can include compression between shoulder and knee during full foot-ground contact, resulting in extension between shoulder and knee during propulsion. In some example embodiments, the ideal bounce further includes associated arm and shoulder movement, wherein the arm and shoulder move lower than a predetermined value during landing, and the arm and shoulder move higher than a predetermined value during propulsion.

In some example embodiments, the ideal bounce can be illustrated through determination of acceleration versus time, such as on a graph or other illustrative tool. In some example embodiments, the ideal bounce can include an impact slope of acceleration versus time which is lower than a predetermined value, representative of the soft landing. In some example embodiments, the ideal running gait or bounce can include an impact period (or width) of acceleration which is wider than a predetermined time value, representative of a gradual bounce or change in the acceleration over time. In some example embodiments, the ideal running gait or bounce can include a peak acceleration which is less than or equal to a predetermined value. In some example embodiments, any of the comparisons between the actual running gait and the ideal running gait values can be satisfied as being within a specified threshold (e.g. 5%), for example, in order to be considered acceptable or good running form. Other features of the ideal bounce will be appreciated in view of the example embodiments described herein.

Reference is first made to FIG. 1, which illustrates a system 100 for training proper running of a user 102 (e.g., a runner), in accordance with an example embodiment. As shown in FIG. 1, the system 100 includes a device 300 and at least one inertial sensor 200 for attachment to an upper body of the user 102. Generally, the device 300 can process sensor data from the inertial sensor(s) 200 to measure movement in relation to gait motion of the user.

More than one inertial sensor 200 can be used in some example embodiments, and can be places at specified locations on the upper body. For example, the inertial sensor(s) 200 can be attached to the chest, upper back, top of shoulders, arms, neck and/or above the waist. As shown in FIG. 1, in an example embodiment, a torso strap 104 is used to mount the inertial sensor(s) 200. In the example embodiment shown, the inertial sensor orientation is mounted parallel to the spine (leaning forward). Additional inertial sensors allow more information to be detected and processed. In an example embodiment, other mounting devices may be used to mount the inertial sensor(s) 200 to the upper body of the user 102, including wristband, watch, necklace, armband, pin, headband, and hat, for example (not shown). In another example, some mobile communication devices such as cellular phones may be equipped with at least one resident inertial sensor or accelerometer, to be mounted in the same example manner as described. In another example, a computer-enabled pair of eye glasses may be equipped with at least one resident inertial sensor or accelerometer. In an example embodiment, inertial sensors are not required for attachment to a lower body of the user 102.

Figure 3:
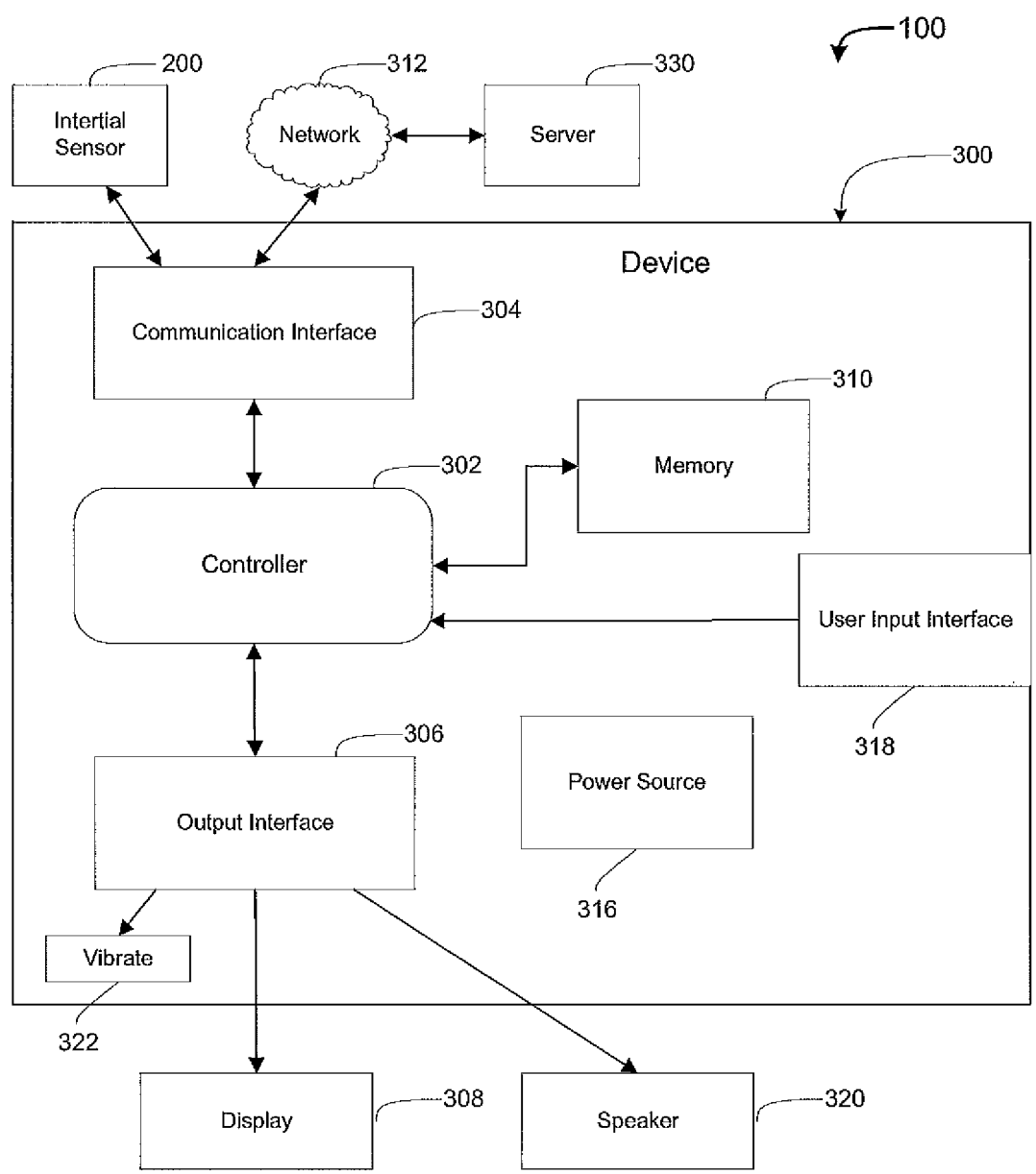
FIG. 3 diagrammatically shows, in block diagram form, details of the system of FIG. 1, in accordance with an example embodiment.

Reference is now made to FIG. 3, which illustrates the system 100 in greater detail, including the device 300 which can for example be a mobile communication device, in accordance with an example embodiment. As shown in FIG. 3, the device 300 may include a controller 302 such as a processor or microprocessor, a communication interface 304, an output interface 306, including a display output for rendering output to a display 308, a tactile or vibrator mechanism 322, and/or a speaker 320 (which can be part of a headphone), for example. In some example embodiments, the display 308 can be resident to the device 300 and/or a secondary display screen. In some example embodiments, the display 308 can be embodied as a computer-enabled pair of eye glasses, or the display of a treadmill, for example.

The communication interface 304 can be configured to communicate over a network 312, such as the Internet, intranet, and/or wireless local area network (WLAN). The device 300 can be configured to communicate with a server 330. As well, a user may be able to access the server 330 through other mechanisms such as through a web portal, dedicated application, etc.

The communication interface 304 can include direct or a short-range communication subsystem, including e.g. infrared, Bluetooth™, ANT, NFC (Near-Field Communications), etc.

In yet other instances, the device 300 may in the form of a mobile communication device, cellular phone or smartphone, tablet computer, laptop computer, a wearable device such as a watch, necklace, wristband, ankle-band, eyeglasses, or other computing device equipped with a communication interface 304. The network 312 can be a wireless network, such as a cellular network or wide area network (WAN), metropolitan area network (MAN), or other such wireless networks.

Input can be made to the device 300 by a user through user input interface 318 using one or more user input devices 324 such as keyboard or keypad, mouse, touchscreen, microphone for voice, etc. In some example embodiments, gesture based inputs may be used, for example through one of the inertial sensors 200 (e.g. when on the arm or hand). The power source 316 can be can be a portable power source such as a battery, which may or may not be rechargeable.

In at least some example embodiments, the memory 310 stores instructions executable by the controller 302 for implementing the processes, functions, or methods described herein. In at least some example embodiments, the memory 310 can also store additional information for an ideal running gait, which may or may not be customized for the particular user. In an example embodiment, the ideal running gait information further includes ideal bounce. In at least some example embodiments, the memory 310 can also store data which is particular to the user such as user characteristics, user activity detected by the sensor 200, and/or sensor data for previous runs as performed by the user (e.g. by date).

Figure 2:
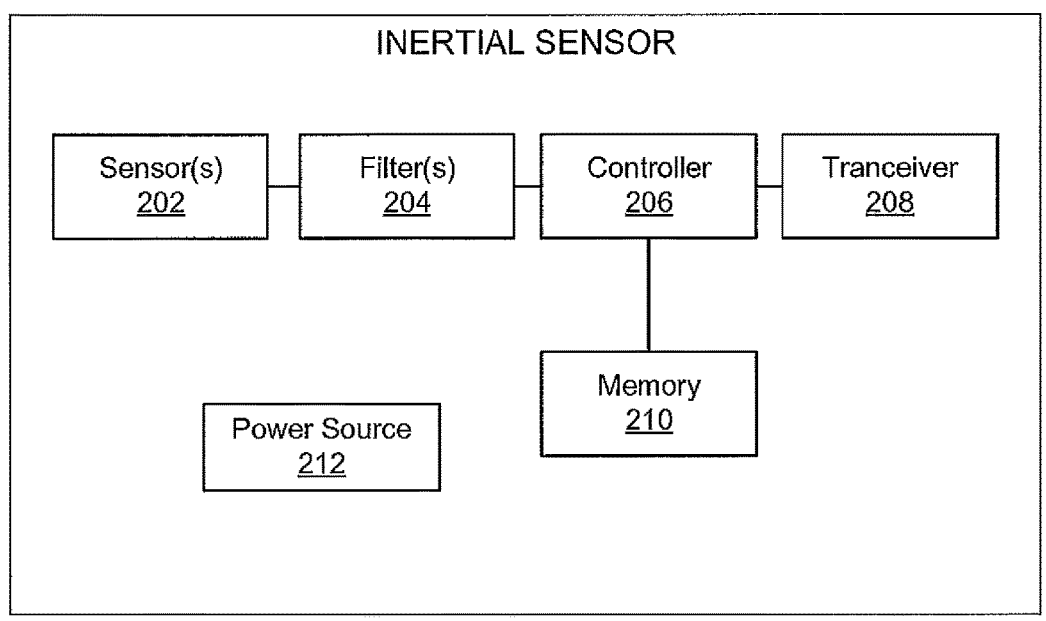
FIG. 2 diagrammatically shows, in block diagram form, an example inertial sensor for use in the system of FIG. 1, in accordance with an example embodiment.

Reference is now made to FIG. 2, which illustrates an example inertial sensor 200, in accordance with an example embodiment. Each inertial sensor 200 can include, for example, one or more sensors 202, filters 204, controller 206, transceiver 208, power source 212, and memory 210. The controller 206 may include one or more signal processors, for example. The controller 206 may have functions or operations performed by or in combination with the controller 302 of the device 300 (FIG. 3), and vice versa. The memory 210 may store information alternatively or in combination with the memory 310 of the device 300 and/or a memory of the server 330 (FIG. 3), and vice versa.

Referring still to FIG. 2, in one example, the sensors 202 include one or more accelerometers. In one example, the accelerometer is at least one of an accelerometer, a tri-axial accelerometer, a gyroscope, and/or a magnetometer. In one example, the power source 212 can be a portable power source such as a battery, which may or may not be rechargeable.

The sensors 202, filters 204, and controller 206 may be integrated together or form discrete elements that may be associated with each other. The controller 206 is operable to analyze measurements provided by the sensors 202 to estimate parameters corresponding to one or more parameter types.

The sensors 202 are operable to measure an acceleration and generate an acceleration measurement corresponding to the measured acceleration, or any related sensor signal indicative thereof. The acceleration measurement may be embodied as a signal operable to be utilized by the filter 204 and/or the controller 206.

In some embodiments, the sensor 200 may be operable to output an analog signal corresponding to an acceleration measurement. For instance, the sensor 202 may output an analog voltage signal that is proportional to measured accelerations. In other example embodiments, the sensor 202 may include any digital and analog components operable to generate a signal corresponding to a measured acceleration. Thus, in some embodiments, the sensor 202 is operable to output a digital signal representing measured accelerations.

In some example embodiments, more than one of the sensors 202 may be integrated into a same integrated circuit package to allow the single package or sensor 200 to provide acceleration measurements along more than one axis. The sensors 202 may include two or more accelerometers operable to output a signal corresponding to a measured acceleration. For example, the sensors 202 may include two accelerometers adapted to measure accelerations in two directions separated by an angle greater than zero degrees and each provide a signal corresponding to the measured acceleration. In some examples, the sensors 202 may include at least three accelerometers adapted to measure accelerations in three directions each separated by an angle greater than zero degrees and each provide a signal corresponding to the measured acceleration. In some embodiments, the three accelerometers may be oriented in a mutually perpendicular configuration. The sensors 202 may include any number of accelerometers, including a single accelerometer positioned in any configuration to provide acceleration measurements.

The transceiver 208 is configured for wireless communication, for example using various radiofrequency (RF) protocols. For example, the transceiver 208 may communicate utilizing Bluetooth, ANT and/or any other wireless protocols.

The filter 204 is operable to couple with the one or more of the sensors 202 and filter acceleration measurements and/or signals corresponding to acceleration measurements. The filter 204 may include analog and digital components operable to filter and/or provide other pre-processing functionality to facilitate the estimation of motion parameters by the processors at the controller 206. In an example embodiment, the filter 204 is operable to filter signals provided by the sensors 202, or signals derived therefrom, to attenuate perpendicular acceleration, to compensate for gravity, and/or to minimize aliasing. The filter 204 may include discrete components for performing each of these filtering functions or use the same components and hardware for these, and other, filtering functions.

The anti-aliasing provided by the filter 204 generally reduces or prevents aliasing caused by sampling of the signals provided by, or derived from, the sensor 202. In some embodiments, the filter 204 includes a relatively wideband filter designed to attenuate signal frequencies in excess of one-half of the sampling frequency used in any subsequent analog-to-digital conversions provided by the controllers 206.

The filter 204 may include any analog and digital components for filtering signals and measurements, including passive and active electronic components, processors, controllers, programmable logic devices, digital signal processing elements, combinations thereof, and the like. The filter 204 may also include an analog-to-digital converter to convert analog signals provided by the sensor 202 to digitize signals for use by the processors at controllers 206 and 44. The filters 204 may also include conventional pre-sampling filters.

The amount of force can be calculated from the sensed acceleration information. For example, this can be calculated as f=m*a (f: force, m: mass of the body, a: center-of-mass acceleration). The mass of the user can be taken into account in these calculations. This can sometimes be akin to Ground Reaction Force (GRF), for example. However, GRF is typically measured using a ground force sensor, and can lose valuable information such as any acceleration which occurs outside of ground impact.

In addition, in an example embodiment, one or more inertial sensors 200 can be used to determine a relative position or amount of displacement, for example using the device 300 as another reference point, for example. In another example embodiment, two or more inertial sensors 200 can be used to triangulate a relative position or amount of displacement, for example using the device 300 a third reference point, for example. Time of flight of wireless signals may also be used, in some example embodiments.

Figure 4A:
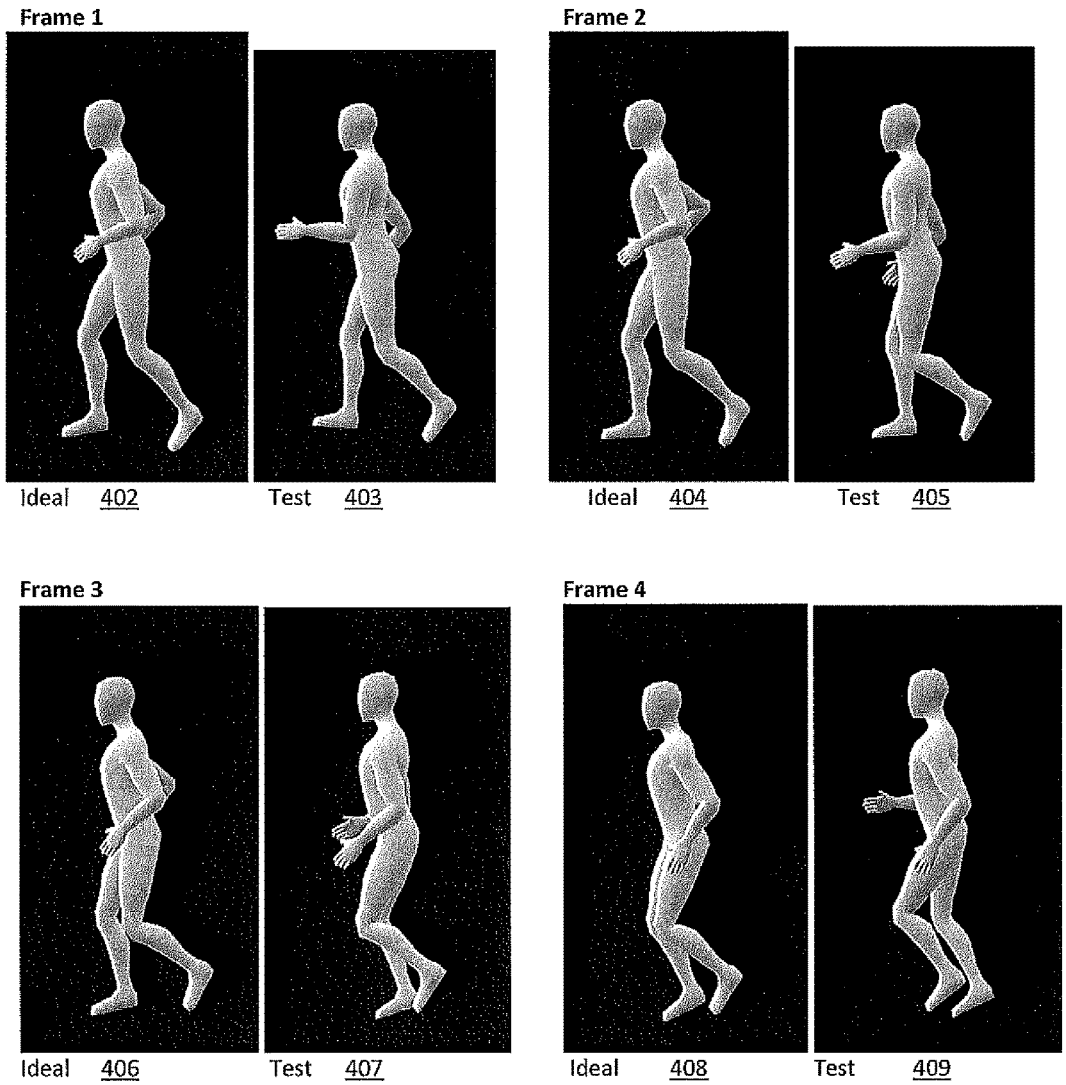
FIGS. 4A, 4B, and 4C illustrate an example animation of an ideal running gait sequence in comparison to a test case, in accordance with an example embodiment.
Figure 4B:
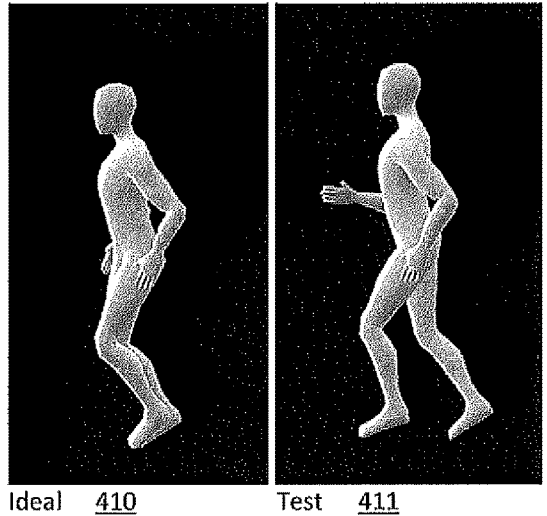
Figure 4B:
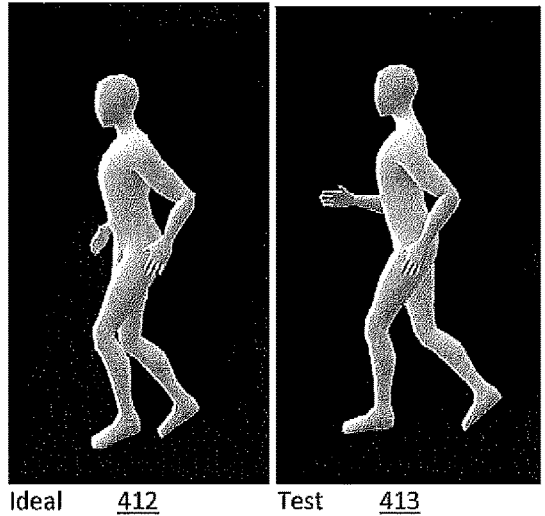
Figure 4B:
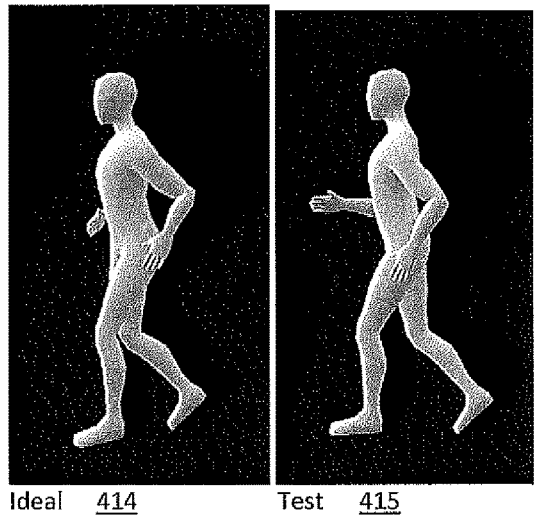
Figure 4B:
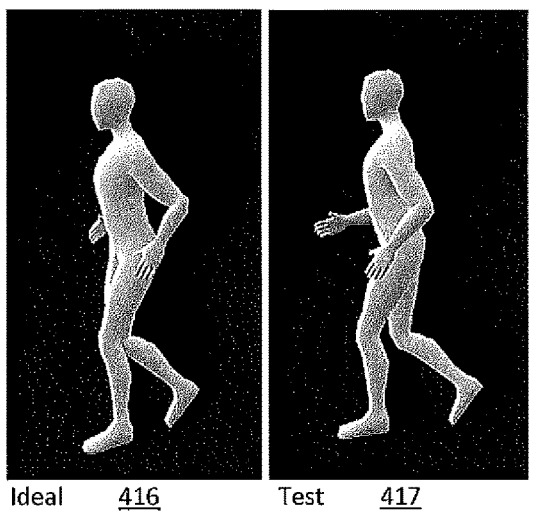
Figure 4C:
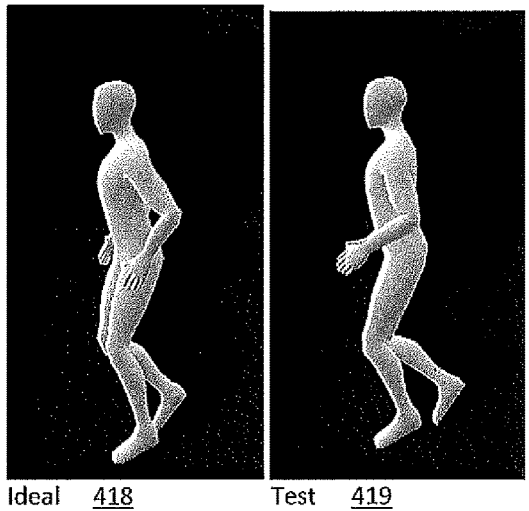
Figure 4C:
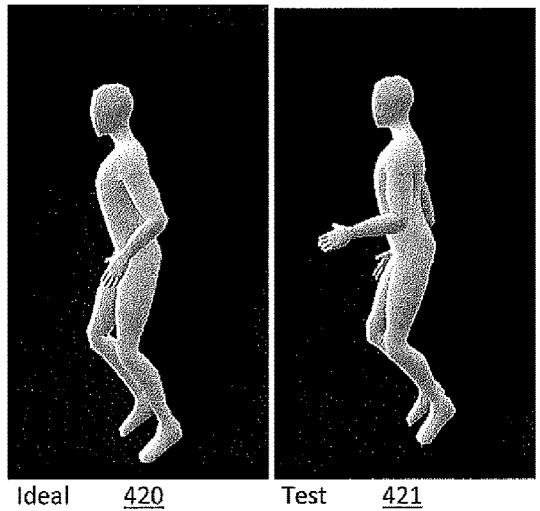
Figure 4C:
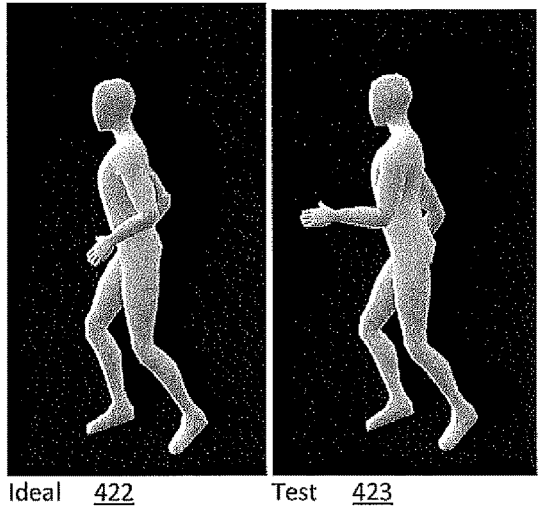
Figure 4C:
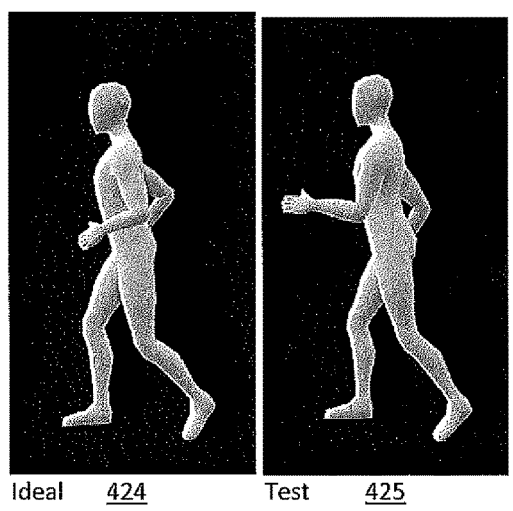

Reference is now made to FIGS. 4A, 4B, and 4C, which illustrates an example animation 400 of an ideal running gait sequence versus an actual running gait sequence, in accordance with an example embodiment. The animation 400 can be at least a part of a displayed user interface on the display 308, to illustrate an ideal running gait versus an actual running gait, for example.

The animation sequence for the ideal running gate includes frames 402, 404, 406, 408, 410, 412, 414, 416, 418, 420, 422 and 424. The animation sequence for the test case running gate includes frames 403, 405, 407, 409, 411, 413, 415, 417, 419, 421, 423 and 425. Note that for the ideal gait case, due to the angle of the camera it appears that the only forefoot of the left foot is touching the ground. In fact, during the major part of landing-compression all part of the foot is firmly or flatly touching the ground.

By way of example only, the four keys phases for running can generally be illustrated as, for the left foot: 1) foot landing, initial contact, which is frame 414; 2) landing impact absorption, which is frames 414 and 416; 3) mid stance, which is frame 416; and 4) propulsion/jumping, which is frames 418 and 420. For the right foot, the four keys phases for running can generally be illustrated as: 1) foot landing, initial contact, which is just frame 404; 2) landing impact absorption, which is frame 404 and 406; 3) mid stance, which is frame 406; and 4) propulsion/jumping, which is frames 408 and 410.

Referring to frames 412 and 414 of the ideal running case, the shoulder and arm are much lower, and upper torso turned slightly left when the foot is about to land. This compressed position body can apply more reaction force, for example, imagine how body will apply the reaction force when jumping off from waist high desk and land. This will allow to land more softly and then can apply stronger reaction force. Using shoulder and arm it is much easier to control the timing, speed and amount of force required for the soft landing.

The above animation frames detail an example ideal running gait animation. Frame 416 illustrates the state of most compressed moment on the right side of the user. Frame 420 illustrates the last state of propulsion using body between shoulder and knee (e.g. toe and heel are still on the ground). The most of the required propulsion is done between frames 416 to 418 to 420.

Additional minor propulsion using the lower leg happens at frames 420 to 422 to 424. If the propulsion between frames 416 to 418 to 420 is weak compared to the required then more propulsion using the lower leg is required between frames 420 to 422 to 424. A common mistake is trying to reduce impact using only legs which results in weaker propulsion between frames 416 to 418 to 420, which causes more propulsion between frames 420 to 422 to 424 resulting in more stress on lower leg.

Still referring to frames 416 to 418 to 420 of the ideal case, stronger propulsion is provided using shoulder and arm from the compressed position. The left shoulder and arm go higher during propulsion and the other right side will goes lower. Using the shoulder and arm, it is much easier to control the timing, speed and amount of force during this propulsion. During this period, the transition from one side of the foot to the other foot is much faster than not using shoulder and aim.

The above major propulsion requires body motion which can be seen, for example, when a person tries to jump from the springboard (e.g. swimming pool spring diving board). Before the jump, the body of the person needs a compression followed by strong propulsion, and usually this requires precise control of timing and amount of force using the upper body.

A similar compression/propulsion required during running can be illustrated by walking with this compression/propulsion (e.g. one side at a time in this case, but similar compression/propulsion). Once a user 102 can learn how to do compression/propulsion at lower speed then he or she can easily apply it at a higher speed (cadence) by making use of the upper body.

Referring to frames 422 and 424 of the ideal case, most of propulsion should be done before this and should not require major force. If the major propulsion was not done previous stage then most likely the lower leg has to apply major force for required propulsion (otherwise body will collapse). This causes more stress to lower leg and can lead to injury.

Figure 7:
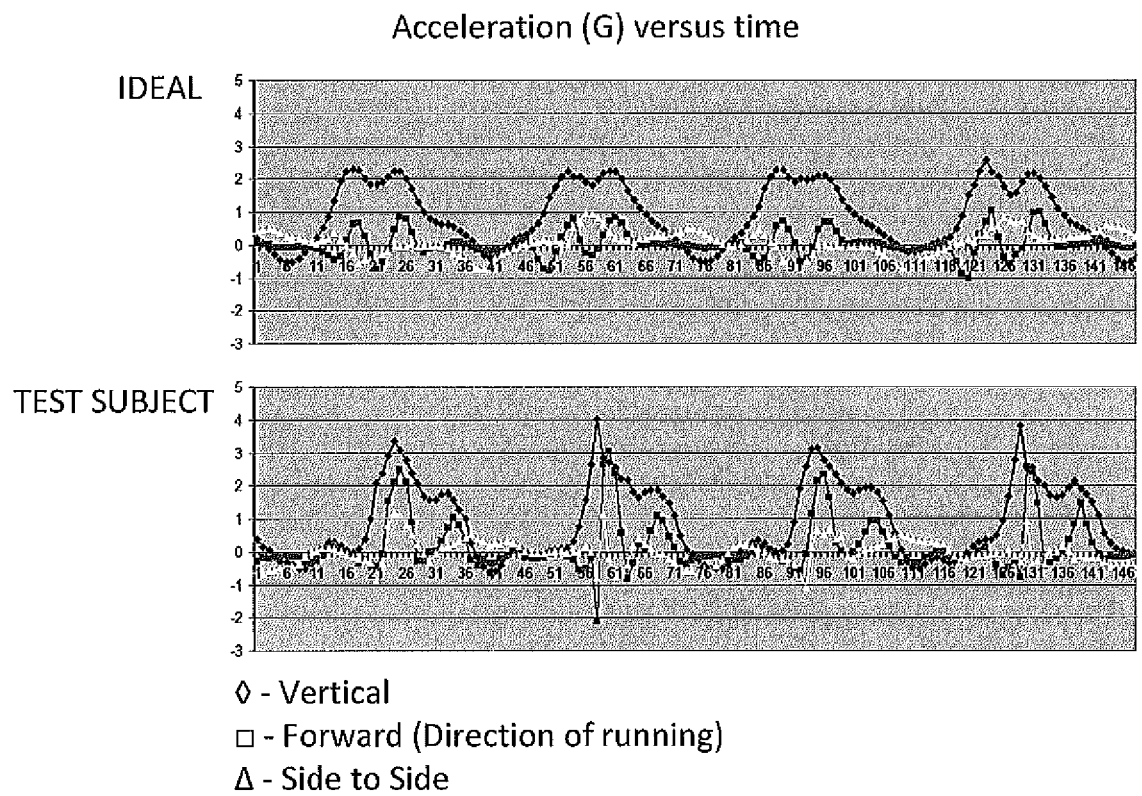
FIG. 7 illustrates example accelerometer readings for comparison of an ideal running gait versus a test case running gait, for all three directional axes.
Figure 8:
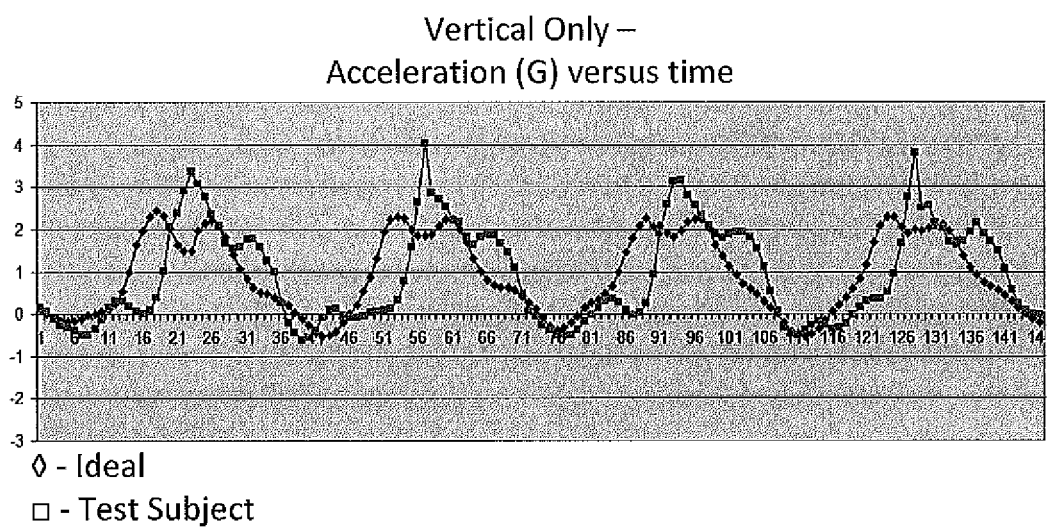
FIG. 8 illustrates example accelerometer readings for comparison of an ideal running gait versus a test case running gait, for the vertical axis only.

Reference is now made to FIGS. 7 and 8, which illustrate example accelerometer readings for comparison of an ideal running gait versus a test case running gait. In FIG. 7, the upper graph represents the ideal case while the bottom graph represents the test subject. FIG. 7 illustrates vertical acceleration represented by diamonds plots, forward acceleration (direction of running) represented by square plots, and side-to-side acceleration (lateral) represented by triangle plots. FIG. 8 represents an overlapped comparison for vertical acceleration only versus time, illustrating the ideal case (diamond plots) versus the test case (square plots).

As per convention, vertical acceleration into the ground is indicated as a positive value, and vice-versa. The test case accelerometer measurements were based from an accelerometer attached to the back of upper torso, based on sensor orientation which is parallel to the spine (leaning forward), and are measured in gravity (G), for example. Measured values are based on sensor orientation which is parallel to spine—leaning forward. The ideal case versus the test case was measured with the same running speed, and similar cadence (steps per min), for example.

As can be observed in FIG. 8, for the ideal case, there is a lower maximum acceleration peak, a slower rising slope for the impact, the positive part is much wider (representing a width of the impact, or period), and there is a narrower negative part. By comparison, for the test subject: there is a much higher peak (up to 4 G, as shown), there is a sharp rise (indicates hard landing), is narrower for the positive part (representing a width of impact, or period), and is wider near the negative part. The negative value represents downward acceleration (which is more than free fall) when shoulder and arm goes up (which pulls down upper body), wherein near zero represents close to free fall, longer free fall means more impact (which requires more GRF, ground reaction force).

Accordingly, in some example embodiments, as can be seen, the ideal running gait or bounce can include an impact slope of acceleration versus time which is lower than a predetermined value. In some example embodiments, as can be seen, the ideal running gait or bounce can include an impact width of acceleration versus time (period) which is wider than a predetermined value. In some example embodiments, as can be seen, the ideal running gait or bounce can include a peak acceleration which is less than or equal to a predetermined value, in this example on or about 2.5 G. In some example embodiments, as can be seen, the ideal running gait or bounce can include a freefall width of acceleration versus time (period) which is narrower than a predetermined value.

Some example embodiments can therefore account for the change is acceleration over time, which is the slope of the tangent (derivative) or which can be referred to as da/dt (a=acceleration; t=time). This can also include readings in the acceleration after impact, which correlates to at least the GRF. The derivative can be calculated for the actual running gait, where anything less than a predetermined value defined by the ideal running gait can be considered acceptable or good form, or e.g. within a threshold thereof, representing a more gradual impact.

As well, some example embodiments can account for the change in the slope itself, which can be referred to as second derivative or $d^2a/dt^2$. This can be used to determine concavity of the acceleration curve over time, which can be correlated to the bounce, width (period) of the impact, or smoothness of the runner (lower slope or rate of change). The second derivative can be calculated for the actual running gait, where anything less than a predetermined value defined by the ideal running gait can be considered acceptable or good form, or within a threshold.

Similar measurements from sensor attached to shoulder/arm (both or just arm) can provide valuable information about how the running gait was shaped. The sensor measurements from torso can be associated with the load (force) to the body's load bearing structure (especially lower leg) based on the f=m*a, the force is proportional to torso (major part of weight)'s acceleration. The measurements from the sensor attached to torso provide insight to the load but does not provide the insight on how it's shaped. As previously mentioned the load can be mainly shaped by the compression/propulsion which can be precisely controlled by movement of shoulders and arms. Analysing the data from sensor attached to arm, for example, can determine how fast and how strong shoulder and arm movement leads the load measured from sensor attached to torso. For example if the user moves shoulder and arm much lower during foot landing and then move them higher with much stronger and faster during propulsion/jump then it will cause much stronger reaction force on that side of the lower body which causes stronger bounce. By comparing the data from sensor attached to arm the system can provide additional information about how to improve running.

Figure 5:
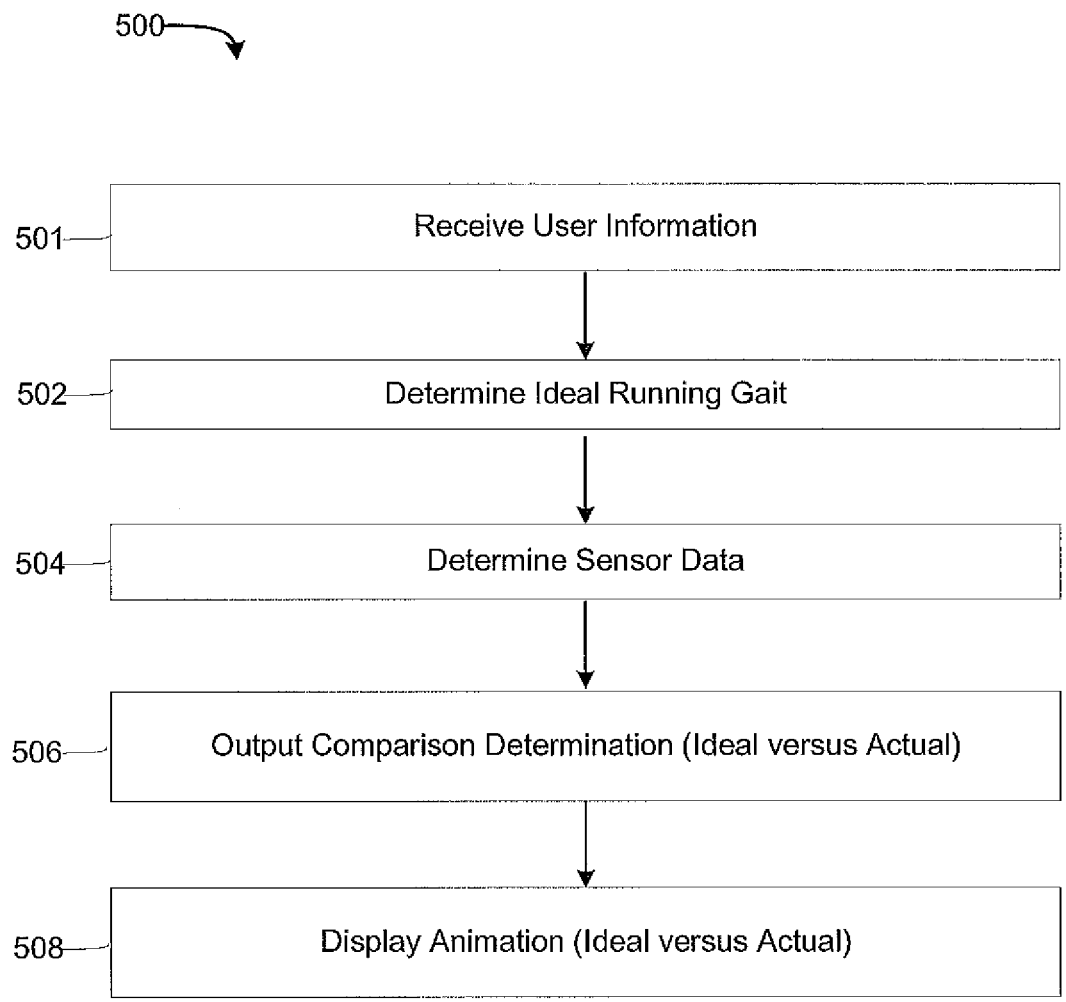
FIG. 5 illustrates a flow diagram of an example method for training proper running of a user, in accordance with an example embodiment.

Reference is now made to FIG. 5, which illustrates a flow diagram of an example method 500 for training proper running of the user 102, in accordance with an example embodiment. The method 500 can be implemented by the controller 302 of the device 300, for example. At event 501, the method can include receiving user information, and can include storing the user information in the memory 310. At event 502, the method 500 includes determining an ideal running gait from the memory 310 including data of an ideal bounce.

At event 504, the method 500 includes determining sensor data from the at least one inertial sensor 200 attached to the upper body of the user 102, for an actual running gait of the user. At event 506, the method 500 includes outputting to at least one output interface 306 a comparison determination of an actual details of bounce of the user 102 with the ideal bounce. The comparison determination can include an indication to perform an action which corrects any discrepancies between the ideal running gait and the actual running gait, typically within a threshold or buffer. In an example embodiment, outputting is performed dynamically by the processor and displayed in real time or near real time. As well, in other example embodiments, sensor data or information for an actual run of the user 102 can be stored in the memory 310, after which the output from the controller 302 can be performed off-line for further review and/or analysis. In an example embodiment, the output is made to at least one of the display 308, speaker 320 (e.g. an audible or voice output generated by the controller 302), and vibrator mechanism 322.

At event 508, the method 500 includes displaying on the display 308 an animation of the ideal running gait and the actual running gait, both simultaneously with cadence synchronized. In an example embodiment, wherein displaying the animation is performed dynamically by the processor and displayed in real time or near real time. As well, in other example embodiments, sensor data or information for an actual run of the user 102 can be stored in the memory 310, after which the displaying at event 508 of the animation can be performed off-line for further review and/or analysis.

In an example embodiment, the outputting of the comparison determination at event 506 is output simultaneously onto the same display 308 graphical user interface screen as the animation (at event 508).

Referring again to event 502, in an example embodiment, the controller 302 can determine the ideal running gait as a generic running gait, generic to any user. In another example embodiment, the controller 302 can determine the ideal running gait using at least some information specific or custom to the user 102. For example, the memory 310 can store user information including at least one or all of: height information, weight information, age information, gender information, personal characteristics (e.g. 3D image renderings), and user preferences. The ideal running gait, and the associated animation, can then be customized by the controller 302 using this information.

Referring again to event 502, in an example embodiment, the controller 302 can further determine an ideal bounce. For example, the controller 302 can additionally output to the output interface 306 a comparison determination or calculation of the bounce between the ideal running gait and the actual running gait. Again, the bounce can be generic to any user, or customized to the particular user 102.

Figure 6:
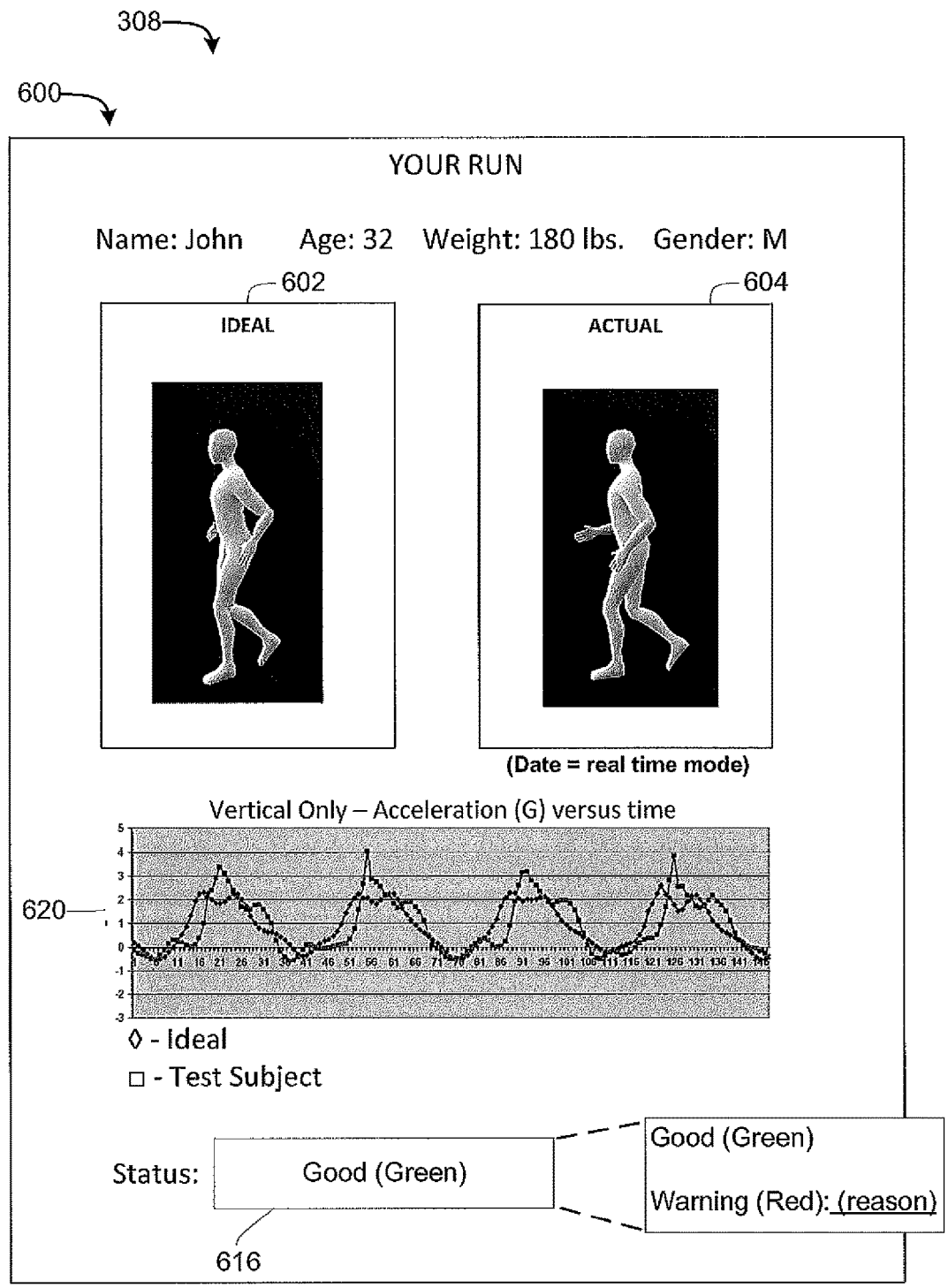
FIG. 6 illustrates an example graphical user interface screen displayed on a display screen, illustrating an animation of an ideal running gait and an actual running gait, illustrating an animation frame at the most compressed moment, in accordance with an example embodiment.

FIG. 6 illustrates an example graphical user interface screen 600 displayed on the display 308, illustrating one frame of an animation of an ideal running gait 602 displayed simultaneously with an actual running gait 604, in accordance with an example embodiment. An example full animation sequence is illustrated in FIGS. 4A, 4B and 4C, for example.

The user interface screen 600 can include more or less elements than those illustrated, in other example embodiments, and depending on the particular application. In addition, some elements of the user interface screen 600 may be provided through other outputs, including a second screen provided on a separate device to the device 300, or the speaker 320, for example. The side-by-side animation can be displayed in real time, near real time, or off-line for review and analysis. The date shown on the screen 600 can be the date and time of a previous run, or in "real time mode", as shown.

As shown on the screen 600, the frames (one shown) for the ideal running gait 602 and the actual running gait 604 are shown simultaneously from the side view, side-by-side, and with cadence synchronized. As described above with respect to FIG. 5, the ideal running gait 602 and the actual running gait 604 can be determined by the controller 302. The frames 602, 604 represent the respective ideal running gait at maximum compression for example, and the synchronized actual user gait at the same running phase.

As shown in FIG. 6, a comparison can be displayed as a graph 620 which illustrates the example accelerometer readings. In an example embodiment, as shown, the example graph 620 can be the same graph as illustrated in FIG. 8. The graph 620 can be updated in real time or near real-time so that the user can be informed of progress of the current actual run. Other graphs can also be shown, such as the graph illustrated in FIG. 7 (not shown here).

As shown in FIG. 6, the comparison determination is output to the user, shown as status 616. A warning (red) can include, for example, when peak vertical acceleration value is over the max threshold (which can be set by user, and/or can be default), below min threshold (lack of bounce also is not desirable), period of near free fall time (from the point where the plot goes now below 0 G to the point where the plot goes above 1 G), associated warning on going over the max which is based on the % of total time for a step cycle and cadence.

Another warning can be output when there is unbalance between left and right, which can be seen in the graph from test subject, as in FIG. 7. The particular type of corrective action can also be displayed on the status 616.

In some example embodiments, as shown, this can be represented by colors (e.g. green for perfect, red for warning), either alone or with associated text. In some example embodiments, a real time or near real time graded score (e.g. A+ to F), or other indicators can be displayed onto the user interface screen 600 to represent the comparison determination.

In some example embodiments, others examples of the comparison determination can be output to the output interface 306 and associated device. For example, audio output can be sent to a speaker 320. The audio output can in the form of a voice output from the controller 302.

In another example embodiment, tactile output can be sent to the vibrate mechanism 322. For example, the vibrate mechanism 322 can be used as a negative stimulus, to vibrate if the actual user is off the ideal cadence or if softer bounce is required, for example. In another example, the vibration can be used as a positive stimulus (for training purposes), for example when the user reaches the ideal amount of bounce, or within a specified threshold, for example. In an example embodiment, the particular output interface 306 can be set (enabled/disabled) via user configuration, and combinations can be enabled to operate simultaneously, for example.

Referring still to FIG. 6, in other example embodiments, the frames are shown as a front view (similar to FIG. 1). Other views may also be implemented, such as side angled view or perspective angled view. In an example embodiment, the particular view can be user configured, with such configurations or preferences stored in the memory 310.

In an example embodiment, rather than side-by-side, the ideal and actual animations are displayed as overlapped animation (e.g., with outline-only, transparency or semi-transparency, for example), with cadence synchronized in real time. In an example embodiment, the animated running motion can be presented with a variety of animated characters. In an example embodiment, the animated running motion can be presented with an avatar or caricature of the user 102, or a 3D image rendering of the user 102, for example. In some example embodiments, the animated characters can be customized over time, for example (but not limited to) showing progress for running speed or weight loss over time.

Some features of off-line review and analysis will now be described in greater detail, with the understanding that some of these features can also be implemented in real-time (when practical). For example, raw or processed sensor data can be collected and recorded in the memory 310, and then the corresponding animation can be replayed later by the controller 302 or any other device. When running outdoors, sensor data from the sensor(s) 200 is collected and stored on the device 300 which is carried during running, and then replayed when the user 102 stops running and replays to see how he/she is running.

In an example embodiment, the user interface screen 600 can be used to show different example animations of the ideal gait motions, such as (but not limited to) warm-up, slow speed running, normal speed running, and fast speed running.

In an example embodiment, the user interface screen 600 can include options for playback/replay at various speeds (e.g., slow motion, normal speed). In an example embodiment, the user interface screen 600 can include exaggeration of key points of gait motion in response to user selection. This can be shown by zooming, or enlarging specified regions of the particular frame 602, such as the torso region. The user interface screen 600 can highlight specific muscles or muscle groups to relax or contract the strength in animation.

In an example embodiment, different (e.g. previous or current) runs can be plotted onto a chart of graph, versus time. For example, the latest run can be shown in comparison to run from a month ago.

The stored data can also be used to calculate important parameters, such as (but not limited to) the runner's impact load, and an estimated sustainable maximum load for the runner.

The analyzed data and calculated parameters can be used to construct an effective and, more importantly, safe training/exercise regimen that can be regularly customized and adapted to the user's evolving skill set and physical ability. In an example embodiment, specific sets of running skills can be evaluated, and grades (rating) can be provided and tracked over time.

The features of the system 100 can be used to teach proper skills of efficient soil bounce during running by making use of the motion capture, animation, and comparison. The system 100 takes the applied load/impact into account and also takes the counter forces (propulsion) into account as well. In the end, the propulsion will be stronger, more efficient and safer by using the stronger parts of the load bearing structures (i.e. the upper body) compared to simply measuring the load/pressure in the lower leg.

In an example embodiment, the user interface 600 and the ideal running gait animation frames 206 can be configured to illustrate strength training exercise programs. For example, this is a way to train and improve key components of compression/propulsion of the user 102. This provides strengthening weight/load bearing structure of the body. As nobody can escape the effects of gravity, strong counter forces are important for running.

The user interface 600 can provide instruction through various means, such as step-by-step commands and instructional illustrations, emphasizing key points of the movements.

In an example embodiment, the user interface 600 and the ideal running gait animation frames 206 can be configured to illustrate how to breath during running. Proper or improper breathing during running can trigger runner's high or headache. Proper breathing can be achieved by controlling upper body, shoulders and arms, for example.

In addition, the system 100 can be used to detect asymmetric gait which can cause more stress on one side, for example.

Reference is again made to FIG. 2 and the server 330. The server 330 can include an application server and/or a web server for providing application services for running training of the user 102, in accordance with an example embodiment. The server 330 can be a remote server implementation, e.g. over the Internet. The server 330 can include a memory, one or more processors and has access to a number of further modules (e.g. applications, application servers, or databases), for example. The server 330 can be in communication with the device 300 and accessible by other devices, over the Internet. The server 330 can store application and software which can be sent to the device 300, for installation by the device 300. The server 330 can store aggregate information for a plurality of users, so that larger scale analysis, trends, improvements can be performed, if desired.

In some example embodiments, the memory in the server 330 stores at least some of the same information as the memory 310 of the device 300, which can be synchronized, for example. The server 330 can collect data specific to the user 102 for further analysis. The server 330 can collect post run logs, analyze gait motion by gender, age, weight, height, frequency of running, distance of running, duration of running, speed of running, for example.

The analyzed data can be used to refine the particular feedback given by the program for more effective instruction. This includes estimating a sustainable maximum load and an amount of time to maintain that load, for the particular user. The maximum load can be determined taking into account the known mass of the user 102 and the amount of detected acceleration. For example, a user could be able to run on Saturday for 1 hour and then run for 1 hour on the next day Sunday without discomfort. The sustainable maximum load increases with proper training, number of runs, length of runs for certain period, for example.

In an example embodiment, by analyzing the data, feedback can be provided to improve technique, such as targeting the utilization (i.e. contraction/relaxation) of specific muscles or muscle groups.

Ratings can be provided for the level of running skills (e.g. blue, red, black belts). In another example, changing animation character can be provided based on run level (e.g. start from fat character to skinny).

In accordance with another example embodiment, there is provided a system for training proper running of a user, including: at least one inertial sensor for attachment to an upper body of the user and configured to provide sensor data; at least one output interface including a display output interface; memory for storing information for an ideal running gait, the information including animation information and including information for an ideal acceleration over time which correlates to at least a GRF(Ground Reaction Force); and at least one processor in operable communication with the at least one inertial sensor, the output interface, and the memory, for executing instructions stored in the memory which, when executed, cause the at least one processor to: determine the ideal running gait information from the memory, determine the sensor data from the at least one inertial sensor for an actual running gait of the user, perform a comparison determination including: whether a rate of change of the actual acceleration of the user during ground impact is less than a predetermined value or within a threshold thereof, and whether a ground impact period of acceleration is greater than a predetermined value or within a threshold thereof, output to the at least one output interface information based on the comparison determination, and display on the display output interface an animation of the ideal running gait and the actual running gait, both simultaneously with cadence synchronized.

In accordance with another example embodiment, there is provided method for training proper running of a user, wherein at least one inertial sensor is for attachment to an upper body of the user and configured to provide sensor data, wherein at least one output interface includes a display output interface, wherein memory is for storing information for an ideal running gait, the information including animation information and including information for an ideal acceleration over time which correlates to at least a GRF (Ground Reaction Force), and wherein at least one processor is in operable communication with the at least one inertial sensor, the output interface, and the memory, for executing instructions stored in the memory, the method being executed by the at least one processor and comprising: determining the ideal running gait information from the memory; determining the sensor data from the at least one inertial sensor for an actual running gait of the user; performing a comparison determination including: whether a rate of change of the actual acceleration of the user during ground impact is less than a predetermined value or within a threshold thereof, and whether a ground impact period of acceleration is greater than a predetermined value or within a threshold thereof; outputting to the at least one output interface information based on the comparison determination; and displaying on the display output interface an animation of the ideal running gait and the actual running gait, both simultaneously with cadence synchronized.

In accordance with another example embodiment, there is provided a non-transitory computer-readable medium containing instructions executable by a processor for training proper running of a user, wherein at least one inertial sensor is for attachment to an upper body of the user and configured to provide sensor data, wherein at least one output interface includes a display output interface, wherein memory is for storing information for an ideal running gait, the information including animation information and including information for an ideal acceleration over time which correlates to at least a GRF(Ground Reaction Force), and wherein at least one processor is in operable communication with the at least one inertial sensor, the output interface, and the memory, for executing instructions stored in the memory which, the instructions comprising: instructions for determining the ideal running gait information from the memory; instructions for determining the sensor data from the at least one inertial sensor for an actual running gait of the user; instructions for performing a comparison determination including: whether a rate of change of the actual acceleration of the user during ground impact is less than a predetermined value or within a threshold thereof, and whether a ground impact period of acceleration is greater than a predetermined value or within a threshold thereof; instructions for outputting to the at least one output interface information based on the comparison determination; and instructions for displaying on the display output interface an animation of the ideal running gait and the actual running gait, both simultaneously with cadence synchronized.

In accordance with an example embodiment, there is provided a non-transitory computer-readable medium containing instructions executable by a processor for performing any one of or all of the described methods.

In the described methods, the boxes may represent events, steps, functions, processes, modules, state-based operations, etc. While some of the above examples have been described as occurring in a particular order, it will be appreciated by persons skilled in the art that some of the steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps may be repeated, as necessary. Elements described as methods or steps similarly apply to systems or subcomponents, and vice-versa. Reference to such words as "sending" or "receiving" could be interchanged depending on the perspective of the particular device.

While some example embodiments have been described, at least in part, in terms of methods, a person of ordinary skill in the art will understand that some example embodiments are also directed to the various components for performing at least some of the aspects and features of the described processes, be it by way of hardware components, software or any combination of the two, or in any other manner. Moreover, some example embodiments are also directed to a pre-recorded storage device or other similar computer-readable medium including program instructions stored thereon for performing the processes described herein. The computer-readable medium includes any non-transient storage medium, such as RAM, ROM, flash memory, compact discs, USB sticks, DVDs, HD-DVDs, or any other such computer-readable memory devices.

It will be understood that the devices described herein include one or more processors and associated memory. The memory may include one or more application program, modules, or other programming constructs containing computer-executable instructions that, when executed by the one or more processors, implement the methods or processes described herein.

The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprises of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

The invention claimed is:

1. A system for training proper running of a user, comprising:
   a mobile communication device including memory, and at least one processor;
   at least one inertial sensor being for attachment to only above a waist of the user, including at least for attachment with an armband, and configured to provide sensor data;
   at least one output interface including a display output interface;
   the memory for storing information for an ideal bounce including i) a landing shoulder and/or arm to knee minimum compression value and ii) a propulsion shoulder and/or arm to knee minimum extension value during ground impact, the information including animation information and including information for an ideal acceleration over time which correlates to at least a GRF (Ground Reaction Force) including an ideal rate of change of vertical acceleration of the user, an ideal ground impact period of vertical acceleration, and ideal propulsion shoulder and/or arm to knee compression and extension during ground impact; and the at least one processor in operable communication with the at least one inertial sensor, the output interface, and the memory, for executing instructions stored in the memory which, when executed, cause the at least one processor to:

determine the ideal bounce information from the memory, determine the sensor data from the at least one inertial sensor for an actual running of the user including actual acceleration, perform a comparison determination between the sensor data and the ideal bounce information including: whether a rate of change of actual vertical acceleration of the user during ground impact is less than a predetermined value, whether a rate of change of the actual vertical acceleration of the user after ground impact is less than a predetermined value, whether a ground impact period of the actual vertical acceleration is greater than a predetermined value, and whether actual landing shoulder and/or arm to knee compression is at least the minimum compression value, and whether actual propulsion shoulder and/or arm to knee extension during ground impact is at least the minimum extension value, output to the at least one output interface information based on the comparison determination, including an acceptable running form indication when it is determined that said comparison determination is satisfied, and display on the display output interface an animation of the ideal bounce and the actual running, both simultaneously with cadence synchronized.

2. The system as claimed in claim 1, wherein the ideal bounce and associated acceleration further includes associated arm and shoulder movement, wherein the arm and shoulder are lower than a predetermined threshold during landing, and the arm and shoulder are higher than a predetermined threshold during propulsion.

3. The system as claimed in claim 1, wherein the ideal bounce and associated acceleration over time further comprises an estimated sustainable maximum amount of load over a specified time period for the user, wherein the at least one processor is further configured to output to the at least one output interface the specified time period or a time remaining from the specified period.

4. The system as claimed in claim 1, wherein the ideal acceleration over time further includes an ideal acceleration for three different axes of acceleration.

5. The system as claimed in claim 1, wherein outputting the information based on the comparison determination includes an indication to perform an action which corrects any discrepancies between the ideal bounce and the actual running.

6. The system as claimed in claim 1, wherein determining the ideal bounce is specific to the user based on at least user information stored in the memory, the user information including at least height information and weight information.

7. The system as claimed in claim 1, wherein the comparison determination includes an indication to the user to maintain the actual running of the user.

8. The system as claimed in claim 1, wherein the at least one inertial sensor includes an accelerometer, a gyroscope, and/or a magnetometer.

9. The system as claimed in claim 1, wherein at least one inertial sensor is part of a torso strap, eyeglasses, band, wristband, and/or necklace.

10. The system as claimed in claim 1, wherein the mobile communication device comprises a mobile phone.

11. The system as claimed in claim 1, wherein the output interface includes at least one of an audio output interface or a tactile output interface, wherein the output includes feedback using audio or vibration, respectively, in relation the information based on to the comparison determination.

12. The system as claimed in claim 1, wherein the comparison determination is displayed on a same display as the animation.

13. The system as claimed in claim 1, wherein inertial sensors are not required for attachment to a lower body of the user.

14. The system as claimed in claim 1, wherein the display output interface is displayed to a display screen of a separate device to the at least one processor.

15. The system as claimed in claim 1, wherein the information for the ideal acceleration over time further includes the following criteria, for the comparison determination:

a peak acceleration which is less than a maximum predetermined value.

16. The system as claimed in claim 1, wherein the information for the ideal acceleration over time further includes the following criteria, for the comparison determination:

a freefall period of acceleration which is less than a predetermined value.

17. The system as claimed in claim 1, wherein the comparison determination further includes determining whether a second derivative rate of change of the actual acceleration of the user during impact is less than a predetermined value.

18. The system as claimed in claim 1, wherein the comparison determination further includes determining whether a concavity of the actual acceleration of the user during impact versus time is less than a predetermined value.

19. The system as claimed in claim 1, wherein the at least one processor is further configured to provide an output when there is unbalance between left and right steps.

20. The system as claimed in claim 1, wherein said displaying on the display further includes displaying, along with the animation, a GRF graph versus time on the display with the stored ideal GRF information and actual GRF information determined from the sensor data, in real time with cadence synchronized.

21. The system as claimed in claim 20, wherein the displayed GRF graph displays a four step cycle of the stored ideal acceleration over time and the actual acceleration.

22. A method for training proper running of a user, wherein a mobile communication device includes memory, and at least one processor, wherein at least one inertial sensor is for attachment to only above a waist of the user, including at least for attachment with an armband, and configured to provide sensor data, wherein at least one output interface includes a display output interface, wherein the memory is for storing information for an ideal bounce including i) a landing shoulder and/or arm to knee minimum compression value and ii) a propulsion shoulder and/or arm to knee minimum extension value during ground impact, the information including animation information, and including information for an ideal acceleration over time which correlates to at least a GRF (Ground Reaction Force) including an ideal rate of change of vertical acceleration of the user, an ideal ground impact period of vertical acceleration, and ideal propulsion shoulder and/or arm to knee compression and extension during ground impact, and wherein the at least one processor is in operable communication with the at least one inertial sensor, the output interface, and the memory, for executing instructions stored in the memory, the method being executed by the at least one processor and comprising:

determining the ideal bounce information from the memory;

determining the sensor data from the at least one inertial sensor for an actual running of the user including actual acceleration;

performing a comparison determination between the sensor data and the ideal bounce information including: whether a rate of change of actual vertical acceleration of the user during ground impact is less than a predetermined value, whether a rate of change of the actual vertical acceleration of the user after ground impact is less than a predetermined value, whether a ground impact period of the actual vertical acceleration is greater than a predetermined value, and whether actual landing shoulder and/or arm to knee compression is at least the minimum compression value, and whether actual propulsion shoulder and/or arm to knee extension during ground impact is at least the minimum extension value;

outputting to the at least one output interface information based on the comparison determination, including an acceptable running form indication when it is determined that said comparison determination is satisfied; and displaying on the display output interface an animation of the ideal bounce and the actual running, both simultaneously with cadence synchronized.

23. A non-transitory computer-readable medium containing instructions executable by at least one processor for training proper running of a user, wherein a mobile communication device includes memory, and the at least one processor, wherein at least one inertial sensor is for attachment to only above a waist of the user, including at least for attachment with an armband, and configured to provide sensor data, wherein at least one output interface includes a display output interface, wherein the memory is for storing information for an ideal bounce including i) a landing shoulder and/or arm to knee minimum compression value and ii) a propulsion shoulder and/or arm to knee minimum extension value during ground impact, the information including animation information and including information for an ideal acceleration over time which correlates to at least a GRF (Ground Reaction Force) including an ideal rate of change of vertical acceleration of the user, an ideal ground impact period of vertical acceleration, and ideal propulsion shoulder and/or arm to knee compression and extension during ground impact, and wherein the at least one processor is in operable communication with the at least one inertial sensor, the output interface, and the memory, for executing instructions stored in the memory, the instructions comprising:

instructions for determining the ideal bounce information from the memory;

instructions for determining the sensor data from the at least one inertial sensor for an actual running of the user including actual acceleration;

instructions for performing a comparison determination between the sensor data and the ideal bounce information including: whether a rate of change of actual vertical acceleration of the user during ground impact is less than a predetermined value, whether a rate of change of the actual vertical acceleration of the user after ground impact is less than a predetermined value, whether a ground impact period of the actual vertical acceleration is greater than a predetermined value, and whether actual landing shoulder and/or arm to knee compression is at least the minimum compression value, and whether actual propulsion shoulder and/or arm to knee extension during ground impact is at least the minimum extension value;

instructions for outputting to the at least one output interface information based on the comparison determination, including an acceptable running form indication when it is determined that said comparison determination is satisfied; and instructions for displaying on the display output interface an animation of the ideal bounce and the actual running, both simultaneously with cadence synchronized.

* * * * *